United States Patent [19]

White

[11] Patent Number: 4,934,336

[45] Date of Patent: Jun. 19, 1990

[54] APPARATUS AND METHOD FOR WARMING INTRAVENOUS EQUIPMENT

[76] Inventor: Steven J. White, 525 N. McKean St., Kittanning, Pa. 16201

[21] Appl. No.: 358,396

[22] Filed: May 26, 1989

[51] Int. Cl.$^5$ .............................. F24J 1/00; A61F 7/12
[52] U.S. Cl. .................................... 126/263; 604/113; 604/408; 128/DIG. 12
[58] Field of Search ............... 126/263, 204, 205, 207; 62/4; 128/68.1, 362, 399, 401, 403, DIG. 6, DIG. 12, 898; 604/113, 408

[56] References Cited

U.S. PATENT DOCUMENTS

| | | | |
|---|---|---|---|
| 2,733,710 | 2/1956 | Zibell | 126/263 |
| 3,550,578 | 12/1970 | Fearon et al. | 126/263 |
| 3,663,335 | 5/1972 | Sheedy | 126/263 |
| 4,077,390 | 3/1978 | Stanley et al. | 126/263 |
| 4,572,158 | 2/1986 | Fiedler | 126/263 |
| 4,573,447 | 3/1986 | Thrash et al. | 126/263 X |
| 4,804,367 | 2/1989 | Smith et al. | 604/113 |

Primary Examiner—Larry Jones
Attorney, Agent, or Firm—Clifford A. Poff

[57] ABSTRACT

An apparatus and method for warming intravenous equipment is disclosed. The apparatus includes at least one warming device comprised of insulated wrap material having at least one removable and reusable heat pack supported along an inner insulated surface of the wrap material. The apparatus releasably encloses intravenous equipment such as I.V. bags and/or I.V. tubing. Two such warming devices can be attached together in series so that one warming device warms the I.V. bag while the other warms a substantial length of I.V. tubing. A flexible insulated strip of material is detachably connected to the wrap material and is used to insulate portions of the I.V. infusion equipment which must be easily accessible and which are neither required nor intended to be heated. The apparatus has particular use for warming intravenous equipment used in routine or emergency pre-hospital situations, especially in cold environments.

15 Claims, 3 Drawing Sheets

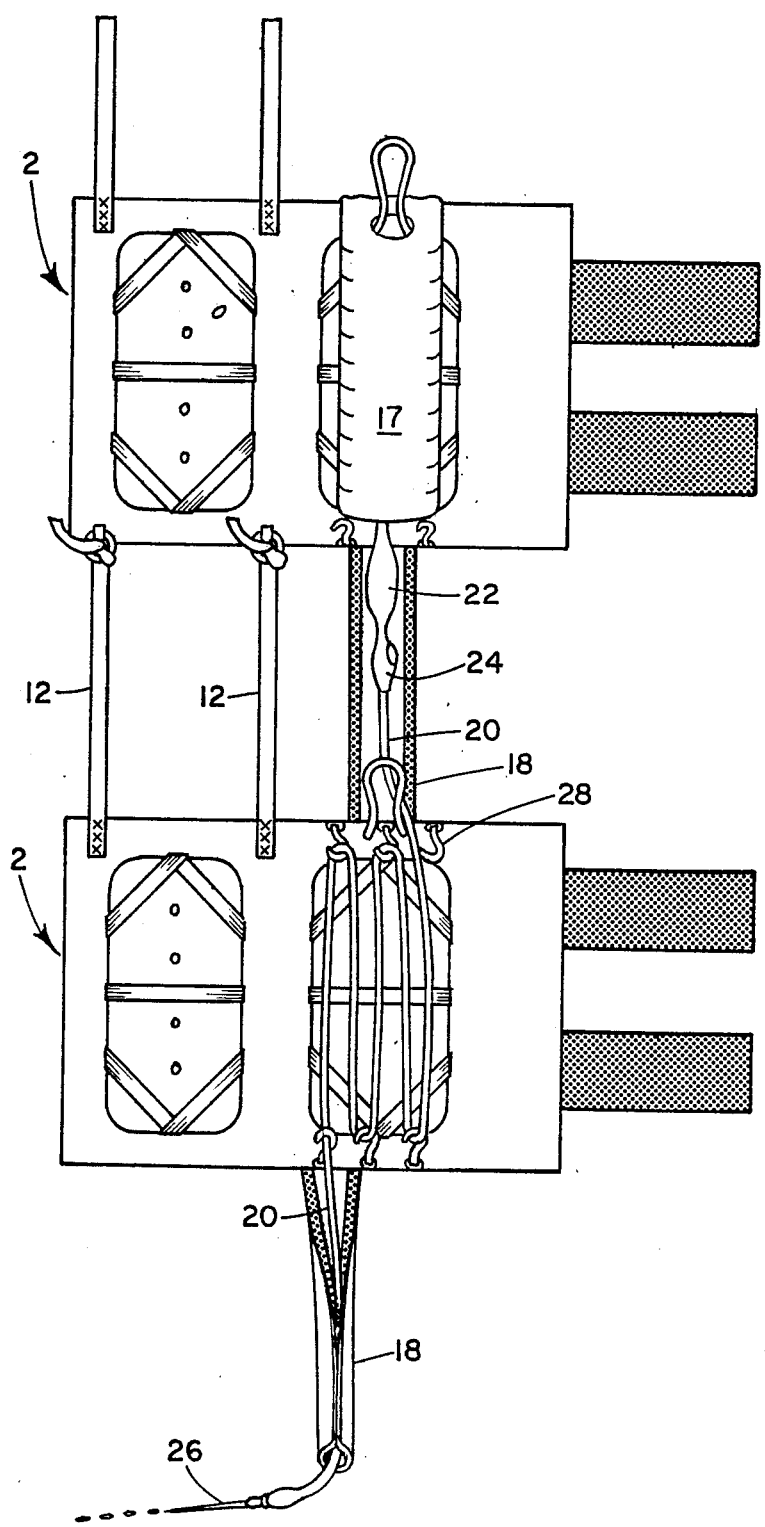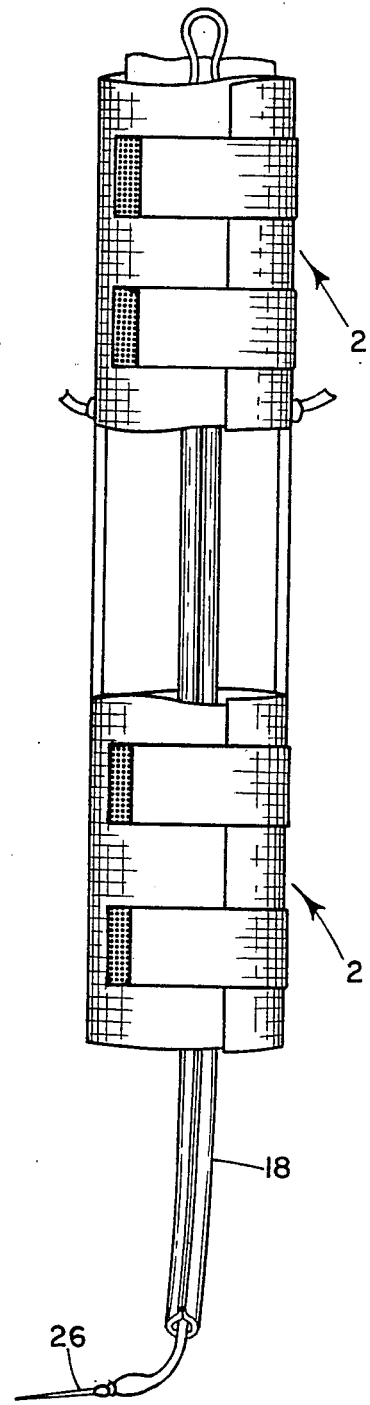
FIG.2
FIG.3

APPARATUS AND METHOD FOR WARMING INTRAVENOUS EQUIPMENT

BACKGROUND OF THE INVENTION

1. Field of the Invention

The present invention relates to heating devices, in general, and to devices for warming intravenous (I.V.) bags and I.V. infusion apparatus, in particular.

2. Description of the Prior Art

In the past, there has been little practical success in the provision of apparatus for warming intravenous (I.V.) medical equipment such as I.V. bags or the like and/or the infusion apparatus used therewith in routine or emergency pre-hospital situations. In many instances there is no need for heating of the I.V. bag and its associated infusion equipment, e.g. when the patient is indoors or in a relatively warm (room temperature or greater) outdoor environment. In emergency situations in cold environments, however, there oftentimes is a great need to quickly and easily heat I.V. equipment in order to rapidly initiate and then maintain a sufficient infusion flow rate of I.V. fluid into a patient. In particularly cold environments, the fluids contained within I.V. bags and/or the infusion apparatus have been known to frequently freeze, especially during intravenous infusion at low flow rates.

A further disadvantage exists in the infusion of insufficiently heated I.V. fluids into a patient suffering from hypothermia, for example. In such a situation, the infusion of I.V. fluids of a temperature which may be even lower than the patient's already potentially dangerously low body temperature may further exacerbate the problem. This would be especially likely when the patient is being treated in a remote, cold outdoor location not readily accessible to shelter, for example.

Attempts have been made to protect or insulate I.V. bags from the effects of cold environments. For example, thermal jacket type devices are known which enclose I.V. bags to insulate the bags. Such devices are useful for maintaining the inherent heat of the I.V. fluid contained within the bag only for relatively short periods of time, especially when under particularly cold environmental conditions. In addition, such devices are of little or no use in actual heating of the fluid within the bag since they do not contain any means for producing heat. Thus, such devices could not be used to reduce the viscosity of, or, if necessary, thaw the fluids within the bags if the fluids had become thickened or even frozen by the cold. Furthermore, such jackets are of no use in warming the I.V. infusion apparatus associated with the I.V. bag.

It is also known to maintain or increase the temperature of fluids in I.V. bags using microwave heaters or the like. Due to their significant weight, bulk and necessity for connection to a sometimes distant energy source, however, such heaters are not at all suited for convenient portability to remote medical emergency sites. Furthermore, the heating energy supplied by such devices is not always readily predictable or controllable. Therefore, the fluid in an I.V. bag heated by such devices, particularly in cold environments, may not become properly heated or, even worse, overheated and destroyed by the heating energy supplied by the heating device.

Advantages exist, therefore, in equipment for warming I.V. bags and/or associated infusion apparatus which is lightweight and portable, does not require attachment to an energy source, is predictable and hence controllable in heat output, and is uncomplex and simple in construction.

It is therefore an object of the invention to provide apparatus for warming I.V. equipment including I.V. fluid-containment means such as fluid bags or the like and/or the I.V. infusion equipment used therewith.

It is a further object of the invention to provide apparatus for warming I.V. equipment, such apparatus being lightweight and portable.

It is a further object of the invention to provide apparatus for warming I.V. equipment, such apparatus requiring no connection to a remote energy source.

It is a still further object of the invention to provide apparatus for warming I.V. equipment, such apparatus being predictable and controllable in its heat output.

It is yet a further object of the invention to provide apparatus for warming I.V. equipment, such apparatus being simple and inexpensive in construction.

It is a further object to provide a method for heating I.V. equipment in routine or emergency pre-hospital situations, particularly in cold environments.

Still other objects and advantages will become apparent in light of the attached drawings and description of the invention presented hereinbelow.

SUMMARY OF THE INVENTION

In accordance with the present invention, there is disclosed equipment which is useful for warming intravenous (I.V.) fluid bags or the like and/or the infusion apparatus used therewith. The equipment includes at least one device formed of a nylon wrap which is lined and insulated with THINSULATE ®. THINSULATE ® is a registered trademark of the 3M Corporation for a class of lightweight fabric materials possessing superior insulation properties. At least one, and preferably two or more, reusable flexible heating packets are replaceably retained within the insulated nylon wrap by a plurality of elastomeric straps. The heating packets are activated to generate heat, then inserted within the elastomeric straps, and then the wrap is wrapped, as desired, around the I.V. fluid bag, or the like, or the I.V. infusion apparatus. The wrap is retained in the wrapped position by snaps, velcro closures, etc. Depending from the wrap may be at least one detachable insulated at least one detachable insulated nylon strip having velcro closures along its length. The detachable insulated nylon strip serves to enclose in a tubular fashion an exposed length of I.V. tubing thus permitting a degree of freedom for reaching the desired, or at least the best available, I.V. needle insertion site on the patient. The wrap is further provided with straps and loops or related fastening means for connecting more than one of the devices in series, i.e., when it is desired to use one of the devices to warm the I.V. fluid bag and at least one other similar device for warming the I.V. infusion apparatus. The device further includes a cord means for supporting the I.V. bag therewithin and also acting as a hanger member for the device. Along the interior of the device there may be provided opposed eyelet means or snap closures between which infusion apparatus such as flexible I.V. tubing can be laced for warming thereof when the wrap is enclosed therearound.

BRIEF DESCRIPTION OF THE DRAWINGS

FIG. 2 is an elevational view of a first embodiment of the warming equipment of the present invention illustrating a pair of warming devices connected in series and in an open position;

FIG. 3 is an elevational view of the equipment of FIG. 2 shown in a closed position.

DESCRIPTION OF THE PREFERRED EMBODIMENTS

Figure 1:
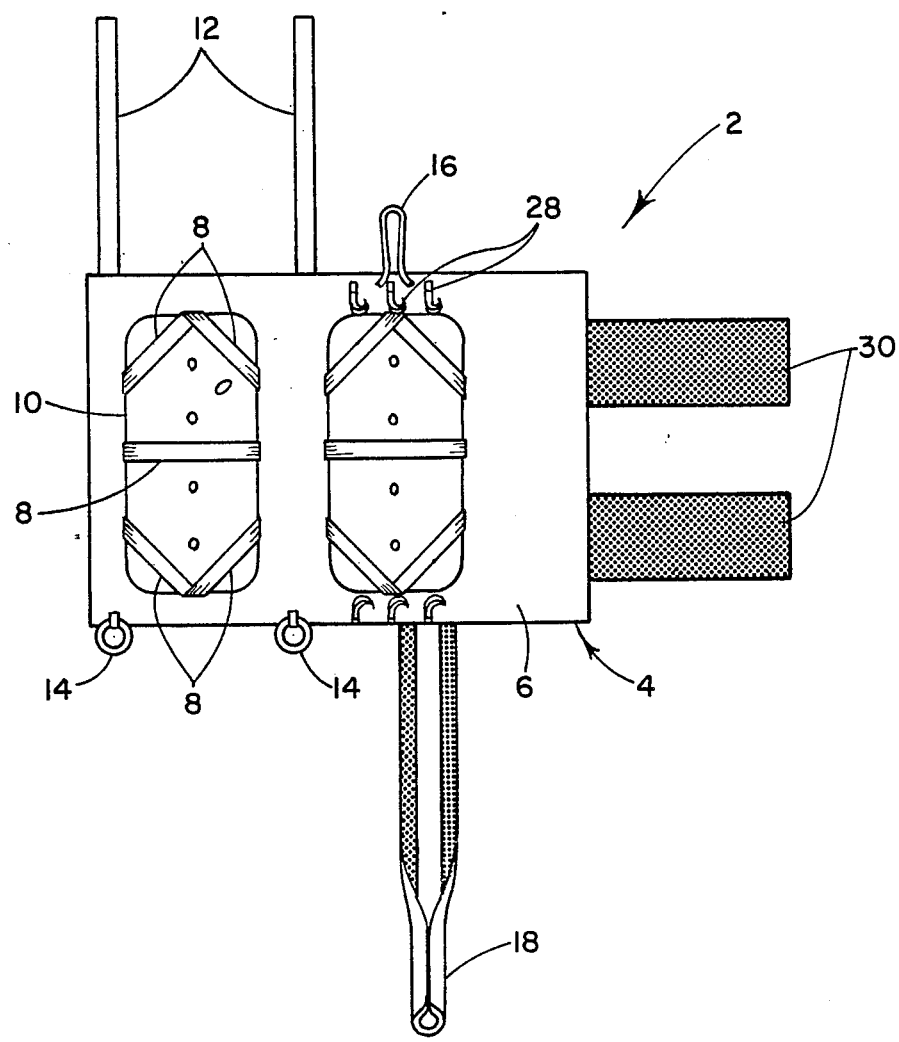
FIG. 1 is an elevational view of a first embodiment of the warming equipment of the present invention in an open position.

Depicted in FIG. 1 is a view of a first embodiment of the invention showing one of the warming devices 2 for warming either intravenous (I.V.) bags, or the like, or I.V. infusion equipment such as I.V. tubing. The warming device includes a substantially rectangular wrap material 4, preferably formed of a lightweight durable synthetic material such as nylon. The wrap material 4 is preferably lined on its interior surface with thermal insulating material 6 such as, for example, THINSULATE ®. The wrap material 4 can be formed of a single piece of material having dimensions of approximately 20" by 14" such that, when folded, it can surround at least 1 liter sized I.V. bags or similar containers. Although not shown, it is also contemplated that the wrap material 4 can be formed as two separate and smaller substantially rectangular pieces of material joined by flexible tether means such as elastic straps, for example. Continuing, it can be seen that the interior surface of the wrap material 4 is further provided with a number of straps 8, which are preferably elastic straps, for replaceably retaining at least one and preferably two heating means in the form of heat packs 10. While any suitable type of relatively small and portable heat packs may be used, the preferred heat packs 10 for use with the present invention are of the class of reusable and rechargeable heat packs disclosed in U.S. Pat. Nos. 4,077,390 and 4,572,158 and formed of a crystalizable supercooled aqueous salt solution encased in a preferably flexible container. The solution may be of any suitable variety of chemical compositions which as they crystallize give off heat through the flexible container. Various solutions such as sodium acetate and calcium nitrate tetrahydrate are examples such solutions. The temperature as well as the duration of heat given off by such packs is accurately predictable and is controlled merely by the concentration of the aqueous salt solution in the pack. Thus, different heat packs formed in accordance with the above-mentioned design having various heat outputs and heat duration times may quickly interchanged in the warming device of the present invention depending on, inter alia, the ambient temperature, the temperature of the patient, and the heat requirements of the I.V. fluids to be infused. However, since any suitable type of small and portable heat pack may be used and since the specific designs of the heat packs 10, per se, do not form part of the present invention, further description thereof is considered unnecessary.

Still referring to FIG. 1, there can be seen extending from along an upper edge of the wrap material 4 a pair of first fastening means preferably in the form of nylon straps 12. Straps 12 are approximately 12" long and are secured to the wrapping material 4. The straps 12 are designed to engage with and be detachable from second fastening means such as ring members 14 which are secured along a lower edge portion of the wrapping material 4 of a similar warming device 2. The provision of the first and second fastening means permits the warming devices 2 to be connected in series so that one of the devices 2 may be used to warm an I.V. bag or similar container while a second of the devices 2 may be used to warm the I.V. infusion apparatus associated with the I.V. bag. Explanation of such a system is presented in greater detail hereinbelow in the descriptions of FIGS. 2 and 3.

The wrap material 4 further has a suspending means 16 secured to an upper portion thereof. The suspending means serves to maintain the vertical position of an I.V. bag 17 within the warming device 2. The suspending means 16 can be formed of either flexible or rigid material so long as it can pass through the hanger hole in the I.V. bag 17 and can be used to suspend and support, in an elevated fashion, the weight of at least a small series of the warming devices 2, including the I.V. bags and/or the infusion apparatus contained therein.

Detachably secured to a lower edge region of the wrap material 4 is a means 18 for insulating portions of the I.V. infusion apparatus which should at all times be quickly and easily assessable and which are not normally required nor intended to be enclosed within the wrap material 4. As can be most clearly seen in FIG. 2, the insulating means 18 is used to insulate I.V. infusion apparatus including I.V. tubing 20, drip chamber 22 and metering means 24. The insulating means 18 preferably is formed of a strip of insulated, preferably nylon, material having velcro fastening means along its longitudinal edges. By virtue of the velcro fastening means, the insulating means 18 can be formed into a tubular enclosure about the exposed I.V. infusion apparatus to protect it from cold weather environments. A similar insulating means 18 can insulate a major portion of the I.V. tubing 20 leading to the I.V. needle 26.

A plurality of eyelet means 28 are provided on the interior surface of the wrap material 4. The eyelet means 28 permit serpentine lacing of a desired length of I.V. tubing 20 therebetween. The eyelet means 28 may be so arranged as to permit either vertical or horizontal lacing of the tubing 20 within the warming means 2. The eyelet means 28 thus serve as a means for supporting a maximum length of tubing within the warming device such that when the heat packs 10 are activated and the warming device 2 is closed, a maximum length of I.V. tubing 20 is warmed within the warming device 2 rather than being exposed to the colder ambient environment thus ensuring a continuous flow through the tubing, even at low flow rate conditions. At least one and preferably two velcro securing straps 30 are secured to the exterior surface of the wrap material 4 of each warming device 2 so that the warming device 2 can be completely and securely enclosed about the I.V. bag 17 and, if desired, the serpentine length of I.V. tubing 20.

As can be seen in FIGS. 2 and 3, each of the warming devices 2 is constructed in substantially the same manner. With such a construction, each warming device 2 can interchangeably be used to warm either the I.V. bag 17 or the serpentine length of I.V. tubing 20. When connected in series as shown in FIGS. 2 and 3, the warming devices 2 serve as a complete equipment system for warming both an I.V. bag and all of the I.V.

infusion apparatus associated therewith with the exception, of course, of the most distal end of the I.V. tubing 20 which carries the I.V. needle 26.

Figure 4:
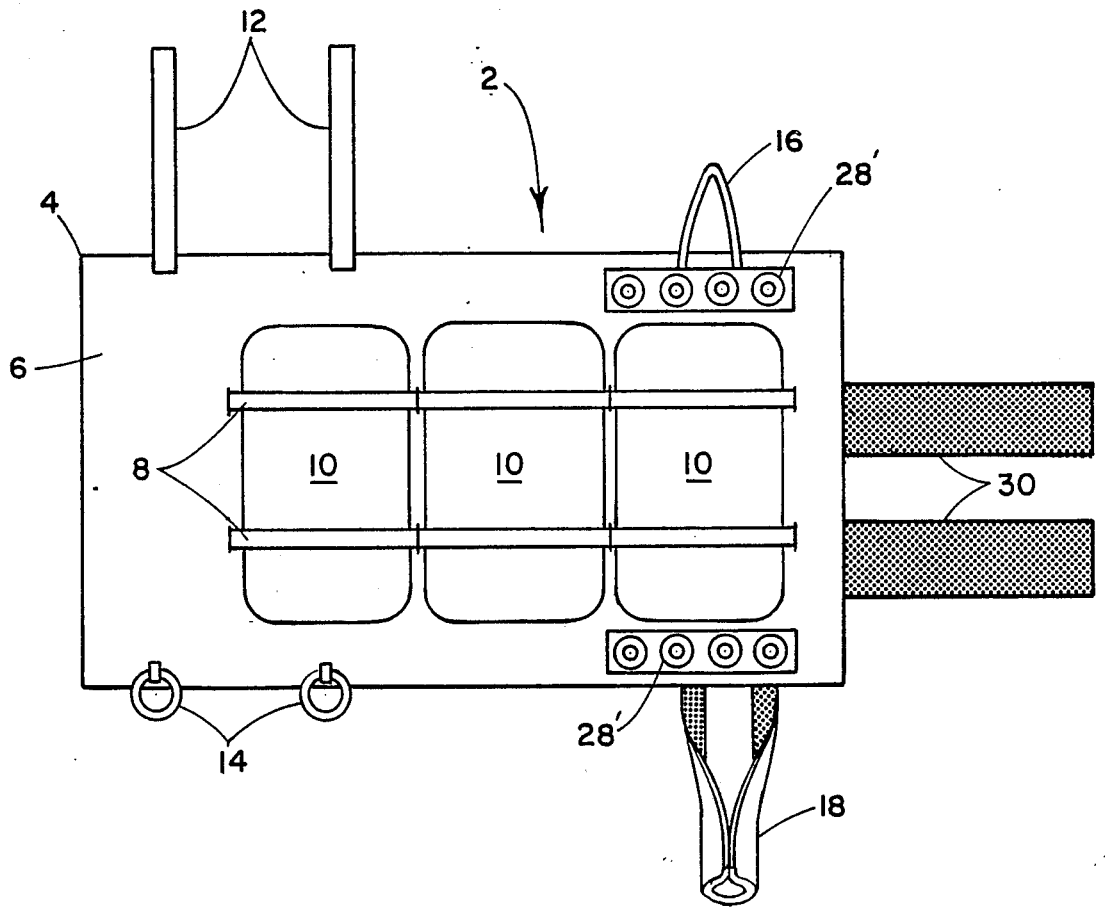
FIG. 4 is an elevational view of a second embodiment of the warming equipment of the present invention in an open position.

In FIG. 4, where like references indicate similar elements, there is illustrated a second and most preferred embodiment of the warming device 2. The FIG. 4 embodiment is preferred over the FIG. 1 and FIG. 2 embodiments because it provides a more complete coverage of the I.V. bag to be warmed therein. As can be seen in FIG. 4, there are three rather than two heat packs 10 in warming device 2 and they extend along virtually the full width of the wrapping material 4 so that when folded around an I.V. bag 17, they serve to provide direct heating contact with all regions of the I.V. bag, including the side seams thereof. The embodiment of FIGS. 1 and 2, on the other hand, illustrates heat pack arrangements which can only provide direct heating contact with the front and back surfaces of the I.V. bag 17 when the warming device 2 is enclosed therearound.

The FIG. 4 embodiment also includes means 28' for supporting a serpentine length of I.V. tubing within the warming device 2. Means 28' are formed as snap closure means. When formed as snap closures, means 28' permit not only serpentine lacing of an I.V. tubing therebetween but they also serve as a secondary type of securement means which work in cooperation with and assist the velcro straps 30 in maintaining complete and secure enclosure of the warming device 2 about either an I.V. bag 17 or a serpentine length of I.V. tubing 20. While not shown, it should be appreciated that the warming device 2 of FIG. 4 can be connected in series with a similar warming device in order to produce a system of equipment for simultaneously warming both an I.V. bag and its associated infusion apparatus in a manner similar to that illustrated in FIGS. 2 and 3.

In all embodiments, the structure of the warming device 2 is formed of commercially available materials and is uncomplicated and inexpensive to construct. It is compact, lightweight and portable, and it further provides rapid yet predictable and controllable heating of I.V. bags or the like and, if desired, the infusion apparatus associated therewith, even in the coldest of environments. It further is completely free of any attachment to a remote energy source for providing energy to its heating source.

Still further, the warming device 2 can be formed of a number of different sizes or as a "one size fits all" size so that it can accommodate small I.V. bags of one-half liter or less to large I.V. bags of one liter or more.

While the present invention has been described in accordance with the preferred embodiments of the various figures, it is to be understood that other similar embodiment may be used or modifications and additions may be made to the described embodiment for performing the same functions of the present invention without deviating therefrom. Therefore, the present invention should not be limited to any single embodiment but rather construed in breadth and scope in accordance with the recitation of the appended claims.

I claim:

1. Apparatus in combination with intravenous equipment, said apparatus comprising:
   wrap material means for enclosing said intravenous equipment, said wrap material means having an interior surface and an exterior surface;
   at least one means for heating said intravenous equipment supported along said interior surface, said means for heating serving to heat said intravenous equipment when said wrap material means is enclosed thereabout; and
   means for releasably enclosing said wrap material means about said intravenous equipment.

2. The apparatus of claim 1 further comprising means for insulating positioned between said interior surface and said means for heating.

3. The apparatus of claim 2 further comprising means for replaceably retaining said means for heating.

4. The apparatus of claim 3 wherein said means for replaceably retaining comprise at least one elastic band.

5. The apparatus of claim 3 wherein said means for heating comprise at least one reusable heat pack.

6. The apparatus of claim 3 wherein said intravenous equipment comprises means for containing a supply of intravenous fluid, said wrap material having means for suspending said means for containing in a position of operable contact with said means for heating, said means for suspending further acting as means for suspending the weight of the apparatus, including any intravenous equipment enclosed therein.

7. The apparatus of claim 6 wherein said intravenous equipment further comprises means for conducting intravenous fluid from said means for containing, said wrap material means having means for supporting a substantial length of said means for conducting in a position of operable contact with said means for heating,
   whereby said means for supporting a substantial length of said means for conducting serves to support a maximum length of said means for conducting within said apparatus and adjacent said means for heating while minimizing the length of said means for conducting left exposed from said apparatus.

8. The apparatus of claim 7 wherein said means for supporting a substantial length of said means for conducting comprising means for permitting serpentine lacing of said means for conducting.

9. The apparatus of claim 8 further comprising means carried by said apparatus for detachably connecting said apparatus in a series arrangement with another apparatus for warming intravenous equipment.

10. The apparatus of claim 9 further comprising means detachably fastenable to said wrap material means for insulating portions of the intravenous equipment not intended for enclosure within said wrap material means.

11. The apparatus of claim 10 wherein said means detachably fastenable to said wrap material means for insulating portions of the intravenous equipment not intended for enclosure within said wrap material means comprise at least one detachable flexible strip having means for fastening along longitudinal side edges thereof,
   whereby said at least one strip is formable into a tubular enclosure for insulating said portions of the intravenous equipment not intended for enclosure within said wrap material means.

12. A system for warming intravenous equipment including at least means for containing a supply of intravenous fluid and means for conducting intravenous fluid from said means for containing, said system comprising:
   a first device for warming said means for containing and a second device for warming a substantial length of said means for conducting, each of said first and second devices having at least one means for heating a respective one of said means for containing and said means for conducting associated therewith; and means carried by said first and second devices for detachably connecting said first and second devices to one another in a series arrangement.

13. The system of claim 12 wherein each of said first and second devices comprise:

wrap material means adapted for enclosure of one of said means for containing and said substantial length of said means for conducting, said wrap material means having an interior surface and an exterior surface, said at least one means for heating being supporting along said interior surface; and means for releasably enclosing said wrap material means about said intravenous equipment, whereby said means for heating heats said intravenous equipment when said wrap material is enclosed therearound.

14. A method for warming intravenous equipment including at least means for containing a supply of intravenous fluid and means for conducing intravenous fluid from said means for containing, said method comprising:

providing at least one wrap material means for enclosing said intravenous equipment, said wrap material means having at least one means for heating said intravenous equipment supported along an interior surface thereof;

wrapping said at least one wrapping material means about one of said means for containing and a substantial length of said means for conducting for enclosure thereof and for permitting heat transfer thereto from said at least one means for heating; and providing means for releasably enclosing said wrap material means about one of said means for containing and said substantial length of said means for conducting.

15. The method of claim 14 further comprising:

providing a second wrap material means for enclosing said intravenous equipment, said second wrap material means having at least one means for heating supported along an exterior surface thereof;

wrapping said second wrapping material means about the other of said means for containing and said substantial length of said means for conducting for enclosure thereof and for permitting heat transfer thereto from said at least one means for heating;

providing means for releasably enclosing said second wrap material means about the other of said means for containing and said substantial length of said means for conducting; and connecting said at least one wrapping material means and said second means in a series arrangement.

* * * * *